United States Patent [19]
Webster

[11] Patent Number: 5,633,414
[45] Date of Patent: May 27, 1997

[54] PREPARATION OF TETRAFLUOROETHYLENE

[75] Inventor: James L. Webster, Parkersburg, W. Va.

[73] Assignee: E. I. Du Pont de Nemours and Company, Wilmington, Del.

[21] Appl. No.: 622,480

[22] Filed: Mar. 25, 1996

Related U.S. Application Data

[63] Continuation-in-part of Ser. No. 414,878, Mar. 31, 1995, abandoned.

[51] Int. Cl.⁶ .................................................. C07C 51/14
[52] U.S. Cl. .......................................................... 570/150
[58] Field of Search ............................................. 570/150

[56] References Cited

U.S. PATENT DOCUMENTS 2,835,711  5/1958  Wolfe ........................................ 260/653
2,941,012  4/1960  Forshey ................................. 260/653.3

*Primary Examiner*—Samuel Barts

[57] ABSTRACT

Metal fluoride and carbon are fed to a plasma flame to form a gaseous reaction mixture which is quenched to form tetrafluoroethylene. The plasma flame can be formed from a non-reactive gas and the metal fluoride and carbon then become part of the plasma flame when fed into it. Alternatively, one of the reactants can form the plasma flame and then the other reactant is fed into it.

21 Claims, 1 Drawing Sheet

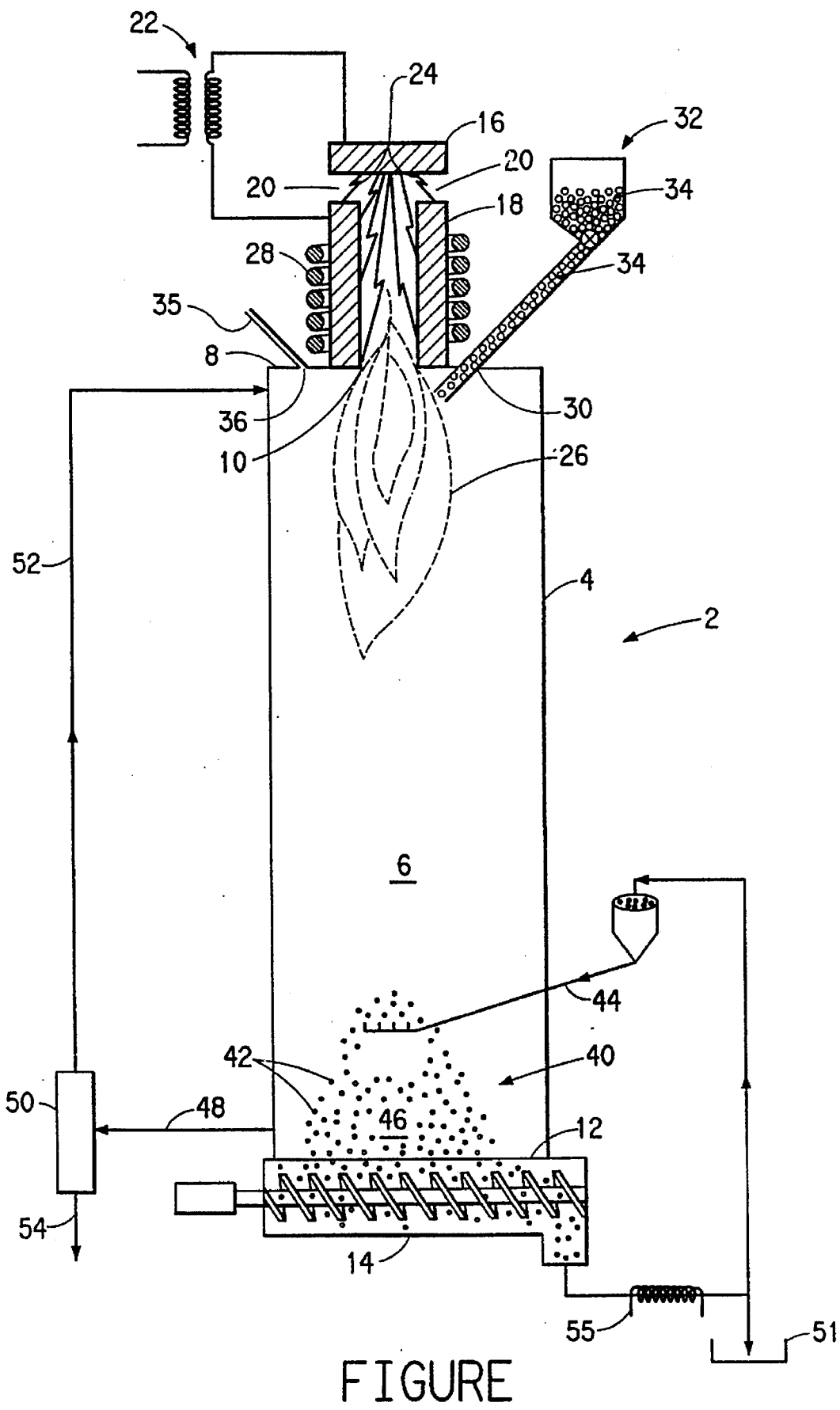
FIGURE

PREPARATION OF TETRAFLUOROETHYLENE

CROSS REFERENCE TO RELATED APPLICATION

This application is a continuation-in-part of application Ser. No. 08/414,878 filed Mar. 31, 1995, by the same inventor now abandoned.

FIELD OF THE INVENTION

This invention relates to a process for the preparation of tetrafluoroethylene.

BACKGROUND OF THE INVENTION

U.S. Pat. No. 2,835,711 (Wolfe et al.) discloses a batch process for reacting fluorides of Group IIA elements of the Periodic Table with carbon to form fluorocarbons which have a variety of utilities, including as intermediates for conversion to tetrafluoroethylene. Only details for high melting Group IIA metal fluorides are given and these involve the melting of the metal fluoride in a crucible by using a carbon arc. Powdered carbon can also be mixed with the metal fluoride in the crucible and the carbon electrodes immersed in the resultant mixture. Gaseous fluorocarbons, primarily $CF_4$, evolve from the resultant melt, leaving behind the reaction product between the metal of the metal fluoride and carbon, which is identified as $CaC_2$ in Example 1.

U.S. Pat. No. 2,709,191 (Farlow et al.) discloses the reaction of silicon fluoride with carbon to produce tetrafluoroethylene at extremely low conversions of the silicon fluoride per pass (Example II) and obtaining increasing proportions of $CF_4$ instead of tetrafluoroethylene at multiple passes (Example I). The "pass" in the process is the passage of silicon fluoride gas at a slow rate through the burning arc struck between two graphite electrodes, and then the gas (reaction product and unreacted silicon fluoride) flows through the hollow bore of one of the electrodes. The carbon reactant of the process comes from the consumable carbon electrode, although carbon powder can also be flowed through the arc with the silicon fluoride. Various operating pressures are disclosed but low pressure (1 to 150 mm of mercury) is disclosed to be preferable. Argon can be used to set the operating pressure, which is then maintained by the silicon fluoride feed. The gaseous reaction mixture is quenched to a temperature no higher than 400° C. within 0.001 to 0.1 sec.

U.S. Pat. No. 2,852,574 (Denison et al.) discloses the pyrolysis of certain Group VA and VIA elements as fluorides or certain organic fluorides to decompose the gaseous fluoride feed at temperatures greater than 1700° C. The pyrolysis is preferably carried out at pressures less than 300 mm Hg by passing the gaseous fluoride starting material through an electric arc struck between carbon electrodes, one of which has a hollow bore, whereby the carbon from the electrodes becomes consumed by combining with the fluorine to form fluorocarbon radicals. The fluorocarbon radicals are passed through the bore of the hollow electrode to contact carbon particles which are at a temperature below 500° C., which quenches the fluorocarbon radicals to favor the formation of TFE over $CF_4$. $CF_4$, however, is disclosed to be a preferred organic fluoride. Together with the TFE and $CF_4$ present in the product stream, the byproducts of the Group VA and VI fluorides are also in gaseous form at room temperature.

The Farlow process has never achieved commercial exploitation for the manufacture of tetrafluoroethylene (TFE) because of the low conversion and low yield giving a generally low production rate of this product. Although Denison achieved higher yields, this process suffered from such problems as difficulty in control of the pyrolysis process by virtue of the electrodes being consumed and low production rate, and thus, this process never achieved commercial exploitation. Instead, TFE has been made commercially worldwide by an entirely different process since the 1950's by a series of process steps, involving (i) reaction of $CaF_2$ with $H_2SO_4$ to form HF, (ii) synthesis of chloroform, (iii) reaction of HF with chloroform to form chlorodifluoromethane (HCFC-22), and (iv) pyrolysis of HCFC-22 to form TFE, and refining the TFE. This series of processes starts with a reactant used in the Wolfe process, but then proceeds on a journey involving the building of four plants ((i) to (iv) above) to arrive at the reaction product of the Farlow process at a high production rate, nevertheless making the manufacture of TFE very expensive, and creating a large amount of HCl byproduct for further processing or disposal.

There has existed a long-felt need for the ability to produce tetrafluoroethylene more economically.

SUMMARY OF THE INVENTION

The present invention satisfies this need by the process for the manufacture of tetrafluoroethylene (TFE) comprising forming an extended turbulent plasma having an undefined portion, dissociating non-carbonaceous metal fluoride into a gaseous mixture of metal and reactive fluorine in the presence of carbon in the undefined portion of said plasma to form a precursor to TFE, and quenching said precursor to obtain as a result thereof said TFE.

In one aspect of this embodiment, the presence of the carbon in the undefined portion of the plasma, i.e., the plasma flame, is obtained by feeding carbon particles into said flame. In another embodiment, the metal fluoride is fed into the flame. In still another embodiment, both the carbon particles and the metal fluoride are fed into said flame and said plasma is obtained from a different material in gaseous form other than said metal fluoride and said carbon.

BRIEF DESCRIPTION OF THE DRAWINGS

The FIGURE shows in schematic cross-sectional side elevation, one embodiment of apparatus for practicing the process of the present invention.

DETAILED DESCRIPTION

The apparatus of the FIGURE will be first described, as an aid to understanding the process of the present invention.

The chemical reactor 2 in the embodiment of the FIGURE is formed from a cylindrical structure 4 to form a reaction chamber 6. The ends of the reaction chamber 6 are formed from a closure plate 8 sealing the top of cylinder structure 4, except for central opening 10 therein, and a bottom opening 12 which feeds an auger 14. The opening 10 forms an inlet to the reaction chamber and the opening 12 forms the outlet to the reaction chamber at its opposite end.

Positioned about the opening 10 are cylindrical electrodes 16 and 18 of opposite polarity and separated by space 20. An electrical power source such as transformer 22 supplies electrical energy with sufficient voltage and current to create and sustain arc 24 struck between the electrodes. A gas is fed under pressure by means such as a blower (not shown) into this arc via the space 20 and is directed into the reaction chamber 6. This flow of the gas through the arc forms a plasma of the gas extending from the arc 24 into the hollow bore of electrode 18, and because the temperature of the arc is thousands of degrees centigrade, the plasma can be considered to be a thermal plasma. The cylindrical electrode 16 may also have a hollow bore (not shown) for feeding gas in the direction of the reaction chamber 6 to direct the overall gas flow into the reaction chamber. This directionality of the gas flow can also be accomplished by feeding the gas through space 20 from multiple locations around the outer periphery of the electrodes. The flow of the gas into the reaction chamber 6 extends this plasma into the chamber.

The portion of the plasma extending into the chamber is shown in the drawing as a plume or flame 26, which is luminous so as to be visible to the eye, and which is directed towards the bottom opening. The flame is not confined to the hollow bore of the electrode 18. The extension of the flame into the cylindrical structure 4 is preferably a free flame in that it is undefined by either the structure 4 or 6. Since the flame extends beyond electrode 18, the flame is essentially free of electric current flowing directly between electrodes 16 and 18. The flame 26, however, may have a small electrical charge resulting from the dissociated gas. Normally the cylindrical structure 4 will be of heat resistant material, such as graphite, and will be cooled. The flame is preferably rotated by magnetic coil 28 encircling electrode 18; this rotation helps cause turbulence within the plasma and helps protect the electrodes from erosion. This turbulence extends into the flame to promote intermixing of the feed material fed into the flame.

An opening 30 is provided in apron 8 to permit feeding means 32 to feed carbon particles 34 directly into the plasma flame 26. The carbon particles are one reactant used in the process of the present invention. Multiple feeding means 32 can be used spaced around plate 8 (and around electrode 18) to enhance the efficiency of the plasma.

The metal fluoride co-reactant for the carbon particles 34 is also supplied to the reaction chamber 6. The flowing gas through the opening 10 into the reaction chamber is either the metal fluoride or is a gaseous material other than the metal fluoride, such as an inert gas. In either case, the gas dissociates in the arc 24 and it is the dissociated species which forms the plasma and its flame 26.

When the flowing gas is not metal fluoride, a line 35 having an inlet 36 in plate 8 is provided for feeding the solid, liquid or gaseous metal fluoride directly into the plasma flame 26 for dissociation therein. Multiple inlet lines 35 spaced around plate 8 can be used. The feed of metal fluoride into the plasma flame can be at high velocity, such as sonic velocity, (maximum flow) to insure that the metal fluoride enters into the interior, i.e., the hottest portion of the plasma flame. In this embodiment, the metal fluoride is a gaseous material, not requiring a solid feed mechanism such as feeding means 32, but such feeding means could be used if the metal fluoride were a solid feed material. Also, use of the inlet 36 for feeding the metal fluoride to the reactor results in this reactant not coming into contact with the electrodes, which may save them from corrosion by the metal fluoride. The feed of carbon particles 34 also does not come into contact with the electrodes, which is a preferred mode of operating the process of the present invention. Both reactant feeds enter into the interior of the plasma flame, where the flame is at its highest temperature, so as to be dissociated in the flame.

A quenching zone 40 is positioned at the outlet end of the reaction chamber to receive the flow of gas from the plasma flame. Within the quenching zone in the embodiment shown are cool quenching particles 42 fed via inlet line 44 as a spray shower directed toward flame 26, with the particles 42 then settling to form a bed 46 thereof, which particles quench instantly the hot gas from the plasma flame to a temperature less than 500° C. The quenching particles are continuously removed from the opening 12 of the reaction chamber 6 via auger 14 for cooling by cooler 55 and recycling to quenching zone via inlet line 44. The cooled gas exits the quenching zone 46 via line 48 where it is subjected to further cooling and separation of desired and undesired product, such as by distillation 50, and the undesired product is recycled to the reaction chamber 6 via line 52, the desired TFE reaction product being recovered in line 54. Multiple lines 52 spaced diametrically around cylindrical structure 4 and aiming into the flame 26 can be used.

From this apparatus arrangement, it can be seen that the reaction chamber forms a reaction zone with the inlet 10 and outlet 12 are oppositely disposed to one another. In this reaction zone, the carbon and metal fluoride are thermally dissociated in the plasma flame and the recombination of the metal and reactive fluorine is prevented by the quenching of the gaseous reaction mixture which action favors the formation of $CF_2$; leading to the formation of TFE upon further quenching. The reactor 2 is preferably positioned so that the gas flow is vertically downward, although the reactor 2 can be disposed differently so as to provide a different direction of gas flow, and the reactor chamber 6 can have many different configurations. In the vertical disposition, any solids that are present in the reaction zone, e.g., undissociated solid reactant, solid reaction products, or solid quench material simply fall by gravity onto the bed 46 for removal by auger 14.

In operation, the metal fluoride is fed to the reaction chamber 6 either via space 20 between the electrodes or via line 35, in which case, preferably a gas is fed through space 20. In either case, the metal fluoride is subjected to the plasma, formed from itself alone or in conjunction with the gas. The plasma flame represents a large volume of plasma. The result is dissociation of the metal fluoride into metal and reactive fluorine present as a gaseous mixture. This gaseous mixture is the flow of gas at this point of the reaction as referred to above. The carbon particles 34 are fed into the plasma flame, whereupon they become gaseous to be part of the gaseous mixture or they become liquid or remain solid until reacted with fluorine from the metal fluoride. The feed location of the carbon particles can be adjusted to various locations within the plasma flame since their physical state is less critical than the dissociation of the fluorine from the metal fluoride.

The result is the formation of gaseous precursor to TFE present in the gaseous mixture, and the TFE is formed by quenching in quenching zone 40 and recovery therefrom via outlet 48 as shown in the FIGURE. The quenching causes the gaseous metal and unreacted carbon to condense, usually to a solid on the quench solids, for easy separation by auger 14 from the still gaseous TFE. The material recovered by auger 14 can contain the quench solids, metal fluorides, carbon, metal from the metal floride, and other non-gaseous by-products. A portion of this material is removed into receptacle 51 for separation and recovery.

The reactions described above and occurring in the process of the present invention can be depicted as follows:

In the plasma:

metal fluoride+C→metal+reactive fluorine+C→metal+CF2    (1)

The formation of $CF_2$: is presumed because of the subsequent formation of TFE when the reaction mixture is quenched.

The quench reaction can be depicted as $$2CF_2: \rightarrow CF_2=CF_2 \quad (2)$$

The process of the present invention provides the following advantages: The metal fluoride starting material can be inexpensive, especially relative to the cost of HCFC-22 which is often the feed source for fluoroolefins. A single plant can be used with relatively low investment. No HCl is produced in the process of the present invention, which simplifies the refinement of the TFE and avoids the need of disposal of the HCl or its further processing for recovery. The desired TFE and other valuable perfuorocarbons can be produced in high yield. The metal of the metal fluoride can be recovered, whereby its value further contributes to the economy of the process of the present invention.

Further details of the process will be described hereinafter.

From the equations (1) and (2) above, the process of the present invention can be simply described as the reaction between metal fluoride and carbon to make TFE. The reaction between metal fluoride and carbon, however, involves the removal of the fluorine atoms from the metal fluoride, i.e., its dissociation. Thermodynamically, as an equilibrium reaction, the reformation of the metal fluoride is to be expected. To make the dissociation reaction occur, the reactants are exposed to sufficient energy which is effective to energize the feed material, i.e., to cause dissociation of at least a portion of the metal fluoride reactant. This dissociation can be into radicals, atoms, and/or ions, which in essence is the excited state for the feed material. In a sense, the reaction is being initiated by dissociation energy being present in the reaction chamber. The plasma is the embodiment of this dissociation energy. As such, the plasma is an energized form of the feed material, whether the plasma is formed from the metal fluoride or is formed from a gas other than the metal fluoride, in which case the metal fluoride also becomes energized when fed into the plasma flame. The metal fluoride is excited to the point that the fluorine from the metal fluoride feed is free to combine with the carbon fed into the plasma flame.

The tendency of the dissociated fluorine and metal in the plasma to recombine can be minimized or avoided by rapidly using up the active fluorine by reacting with an excess of carbon, to form TFE i.e. the gaseous reaction mixture containing the precursor to TFE, the TFE being formed upon subsequent quenching of the reaction mixture. The presence of gas other than vaporized reactants, e.g., a non-reactive or inert gas fed to arc 24 via space 20 between electrodes, to form the plasma is preferred because this retards the recombination of the reactive fluorine with the metal, thereby enhancing the availability of the reactive fluorine for reaction with the carbon in the plasma flame. The gas in effect acts as a carrier for the reactants which dissociate and become part of the plasma, together forming the gaseous reaction mixture fed to the quenching step.

With respect to the starting materials of the process of the present invention, carbon can be obtained commercially from a wide variety of sources. Clearly, the purer the carbon, the fewer the by-products in the process. Water, as much as possible, should also be excluded from the carbon and the source of metal fluoride. Extraneous water allows the formation of HF and metal oxides. It is also preferred that the carbon be deoxygenated so as to not provide oxygen to the reaction system. Exclusion of oxygen from the reaction system avoids the formation of metal oxide byproducts and oxygen-containing fluorocarbons. Carbon particles in the 0.1 mm or less in average size are preferred for ease of handling, reactivity, and potential vaporization.

The metal fluoride can be a compound or mixture of compounds, each of which contains one or more fluorine atoms. It is the fluorine atoms that are the active reactant portion of the metal fluoride, so the metal portion thereof can have a wide range of identities. Examples of metals (as fluoride), or mixtures thereof include lithium, sodium, potassium, magnesium, calcium, chromium, manganese, iron, nickel, copper, zinc, aluminum, boron, and silicon. The preferred metals come from Groups IA, excluding hydrogen, IB, IIA, IIB, IIIA, IIIB, IVA, IVB, VB, VIB, VIIB, and VIII of the Periodic Table (R. H. Perry and C. H. Chilton, *Chemical Engineer's Handbook*, 5th Ed., McGraw-Hill, inside cover (1973)). The metal fluoride can be economically obtained from mining operations, and will be non-carbonaceous (contains no carbon). Metal fluorides used in the present invention are much more difficult to dissociate, and thus be reacted with carbon than fluorocarbons such as $CF_4$ and $C_2F_6$. Generally, the metal fluorides such as $CaF_2$ and silicon fluoride require at least 100% more energy to cause dissociation, which is difficult to achieve in the millesecond contact (exposure) time of the metal fluoride with the plasma flame. One of the reasons for the much greater energy required for dissociating metal fluoride is that a much greater number of chemical bonds need to be broken to make fluoride from metal fluorine available for reaction with carbon. The metal/flourine bond for such metal fluorides as silicon fluoride, calcium fluoride, is also much stronger than the carbon/fluorine bond. In the case of fluorocarbons, some of the carbon/fluorine bonds are already formed, whereby fewer carbon/fluorine bonds need to be broken. Preferably, the metal portion of the metal fluoride has inertness or low reactivity to the carbon or carbon/fluorine moiety (reaction product) under conditions of the reaction.

Preferred metal fluorides include NaF, $CaF_2$ and silicon fluoride such as $SiF_4$, $Si_2F_6$ and metal silicon fluoride such as calcium fluorisilicate. Preferably, the metal fluoride does not contain any other halogen atoms. The presence of oxides in the metal fluoride is less desirable since the oxygen can form less desirable metal oxides including carbon/oxygen compounds.

The present invention having revealed the starting materials and reaction mechanism to be used, one skilled in the art will recognize many ways to subject metal fluoride to a plasma to generate the dissociation energy required. Thus, the reaction can be carried out by producing the dissociation energy by an electrical arc, either A.C. or D.C., using a plasma reactor, or by electromagnetic energy created for example by an induction coil or microwave, or by heating alone. In the case of the electrical arc, the applicator of the dissociation energy is within the reaction zone, as in the case of the FIGURE while in the case of the electromagnetic energy, the applicator of the energy, e.g., an induction coil, can be exterior to the reaction chamber, but creating the dissociation energy within the reaction chamber.

The plasma reactor is one type of apparatus for carrying the dissociation of the metal fluoride to prepare it for the reaction with carbon. The electrical discharge, e.g., arc 24, between these electrodes can be rotated by a coil-induced magnetic field or the arc can be stationary. The electrodes can be, among other materials, of copper and can be water cooled so as to provide long operating time. Preferably, the material of construction of the electrodes is such that the electrodes are not consumed by reaction with the metal fluoride feed. Thus, if the metal fluoride is fed into the plasma flame, i.e., downstream from the arc, cooled carbon electrodes can be used. If the metal fluoride, however, is fed through the arc, then non-carbonaceous material is preferably used as the material of construction of the electrodes. It is the region of the arc that provides the excitation energy useful in the present invention, which manifests itself as intense heat to produce a plasma of material fed to it. The plasma forms a visible glow region extending downstream from the arc, in the direction of the fluid flow within the reactor, which glow area is called the plasma flame, such as flame 26 in the FIGURE.

Measures can be taken, e.g., a rotating electric arc or tangential feeding, to produce a turbulent mixing action in the plasma flame and if desired within the arc, to give high operating efficiency.

The feed material, whether gas, liquid, or solid can be directly or indirectly energized, i.e., subjected to the dissociation energy generated by the rotating electric arc or by other means. An example of direct exposure would be when a reactant feed, such as $SiF_4$, which is gaseous at room temperature (20° C.), is fed to the electrical arc (or the electromagnetic field of a different apparatus). An example of indirect exposure would be when a gaseous non-reactant is fed the arc (direct exposure), and the resultant excited or dissociated gas (plasma) is then brought into contact with the metal fluoride and carbon reactants (indirect exposure) in the plasma flame downstream from the arc. In this embodiment, the plasma can be first formed from an inert gas, such as argon or helium, and metal fluoride and carbon is then added to the plasma flame. The plasma flame is formed from the particular feed material that is directly exposed to the arc in the plasma reactor. Thus, the present invention includes all of these possibilities for subjecting feed materials to the dissociation energy (energizing of the feed materials) of the thermal plasma. These possibilities can be effective to prolong electrode life in the case when one or more of the feed materials are corrosive to the electrodes.

When inert gas is fed to the arc to form the plasma flame and the metal fluoride is fed to the flame downstream from the arc, the amount of inert gas used is preferably an excess with respect to the amount of metal fluoride, so as to provide the energy (heat) needed to dissociate the metal fluoride. Preheating of the metal fluoride enables the amount of inert gas to be reduced. In general, however, at least 5 moles of inert gas/mole of metal fluoride will be used, and excesses such as at least 10 or 20 moles of inert gas/mole of metal fluoride can be used.

The energy used to energize or excite the feed material to form the thermal plasma can generally be quantified by specification of the power input to create the plasma plus the thermal energy available if any of the feed materials to the reaction zone are preheated.

When an electric arc is the source of the plasma, the temperature produced by the arc can be controlled by varying the arc power input and/or the feed rate of material through the arc. For the particular power available from the arc reactor, the flow rate of the feed material is adjusted so that the feed material becomes energized (excited) by this exposure to dissociation energy and becomes part of the plasma. Control of power input and feed rate will also determine the temperature of the plasma created by other electrical means. Fluorine is most tightly bound to such metals as silicon, magnesium, calcium, and aluminum, and less so to metals such as iron, copper, and zinc. In general, less energy (lower temperature) is required to dissociate the metal fluoride when the metal/fluorine bond is weaker. For any particular metal fluoride, lower pressure within the reaction zone, allows the dissociation to occur at lower temperature. The pressure can be sub-atmospheric, such as at least 20 mm Hg, and preferably at least 300 mm Hg, atmospheric, or super-atmospheric. By way of example of the effect of pressure, if carbon tetrafluoride were fed to the plasma, the level of dissociation at atmospheric pressure and 2700° C. would be similar to that obtained at 10 mm Hg and 2200° C. Above about 2800° C., and at atmospheric pressure and equilibrium, $CF_4$ is totally dissociated into $CF_2$: radicals, fluorine, and other carbon and carbon/fluorine related species. It is because of this dissociation and incumbent formation of $CF_2$: radicals that rapid quenching bypasses the reformation of $CF_4$ and other related saturated perfluorocarbons, leading to principally the formation of perfluoroolefins, primarily TFE.

For the range of fluoride starting materials that can be used, along with the range of pressures that can be used, it is believed that the heat present in the creation of the dissociation energy (plasma), the temperature will be at least 3800° C. at atmospheric pressure. More often, the temperature will be at least 5000° C. at atmospheric pressure. Extremely higher temperatures may be used, e.g., even more than 10,000° C. At such temperatures, the metal fluoride, if not gaseous at ambient temperature, is either completely or partially volatilized in the plasma. While temperatures in the range of 5000° C. are required for the total vaporization of carbon, carbon above its melting point and even solid carbon can be in reactive form in the plasma atmosphere. Silicon tetrafluoride is gaseous at ambient conditions and thus provides a convenient feed to the reaction zone. $CaF_2$, e.g., boils at 2500° C. and can, therefore, be present as a gas or mixture of gas and liquid in the reaction zone, depending on the temperature and pressure in this zone. The metal fluoride may thus be present as a mixture of gas and liquid material, again depending on the particular fluoride compound and reaction conditions. Temperatures of about 2000° C. and less can conveniently be measured with a thermocouple. Higher temperatures, especially those of an electrical arc or plasma flame can be determined by known means, usually estimated by mathematical analysis of the power inputs, feed compositions and flow rates.

While the proportion of carbon present in the reaction zone is preferably sufficient to combine with all the fluorine atoms of the metal fluoride so that fluorine atoms are not left over to recombine with the metal to re-form metal fluoride, all of the metal fluoride feed to the plasma flame need not react with the carbon in a single pass through this zone. It may be desirable to react only a portion of the metal fluoride in a single pass through the zone and to recycle unreacted metal fluoride to the reaction zone for further conversion. Preferably, however, the reaction is conducted so that a single pass is sufficient, wherein at least 50% of the metal fluoride is stripped of its fluorine and more preferably, at least 85%, and even more preferably, at least 90%. Preferably, excess carbon is present to favor the formation of $CF_2$ and ultimately TFE, whereby at least 1 atom of carbon is present for each atom of fluorine, and more preferably at 2 atoms of carbon for each fluorine atom.

The reaction mixture is cooled rapidly to a temperature less than 500° C., to obtain TFE, and relatively small amounts of higher perfluoroolefins, notably hexafluoropropylene (HFP) and desirable saturated perfluorocarbon. The saturated perfluorocarbon could contain at least 2 carbon atoms, such as hexafluoroethane. TFE is the preferred reaction product and is preferably present to constitute at least 60 wt % of the perfluorocarbon obtained from the convened metal fluoride, more preferably at least 80 wt %, and even more preferably, at least 90 wt %. The rapid cooling (quenching) is preferably carried out at a rate greater than 10000° C./sec.

When the metal of the metal fluoride is silicon fluoride, the silicon recovered, e.g., from the quenching zone 40 shown in the FIGURE, can be of good purity, making this a valuable byproduct of the process of the present invention although further purification may be desirable for specific applications. Recovery of silicon can be enhanced by the quench particles 42 therein being cooled silicon particles. The silicon from the reaction condense on these particles, just increasing their particle size but without causing the silicon particles to stick together because of the rapid quenching of the silicon through any liquid state. The resultant larger silicon particles can be removed from the zone 46 by auger 14 for cooling via cooler 55 and recycled to the chamber for additional silicon growth. As the silicon particles grow too large, they can be removed by screening during the recycling step and collected in receptacle 51, and small particles of additional silicon added as make-up in the quenching chamber. The removed particles can be refined to separate the silicon from any carbon and other by-products that may condense on the quench particles. When other metal fluorides are used, the quench particles can be of the same metal to minimize separation difficulties.

In another embodiment, particles 42 of other solid materials, such as carbon, can be used in the quenching chamber, and the condensed metal can then be separated by conventional means from such other solid material particles. The formation of SiC is minimized or avoided in the bed 46 of carbon particles by the short exposure time and rapid quenching. The particles 42 do not have to contain carbon and thus can be non-carbonaceous. Gases and/or liquids can also be used as part or all of the quenching medium.

The presence of any non-gaseous materials in the plasma will simply fall into the bed 46 of quenching particles to be collected in the auger 14. The metals condensed from the gaseous reaction mixture in the quenching zone may be in liquid form but will more often be in the solid form, depending on the particular metal of the metal fluoride feed to the process. As reference points, the boiling point of carbon is 4827° C., silicon is about 2350° C., calcium is 1480° C., calcium fluoride is 2500° C., silicon tetrafluoride is −86° C., and silicon dioxide is 2330° C. Melting points of these materials are as follows: carbon about 3550° C., silicon 1410° C., calcium 840° C., calcium fluoride 1420° C., silicon tetrafluoride −90° C. and silicon dioxide 1720° C.

The desired perfluoroolefins and desired saturated fluorocarbons are separated from the reaction product by any variety of methods known to those skilled in the art, including distillation, adsorption, or absorption. Undesired fluorocarbons, any unconverted metal fluorides and any undesired perfluoroolefins can be recycled to the plasma or simply into the reaction zone, such as reaction chamber 6 via inlet line 52 in advance of the reaction with carbon. For example, when $CF_4$ is produced as a byproduct of the process, this fluorocarbon can be recycled to the plasma via line 52. Usually, the amount of $CF_4$ present in the fluorine/carbon reaction mixture after quenching will be less than 40 wt % based on the total weight of fluorocarbon present, more preferably less than 20 wt %, and even more preferably, less than 10 wt %.

EXAMPLE 1

The desired reaction sequences are as follows:

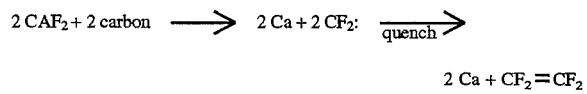

At atmospheric pressure, 140 grams/minute of argon is energized by passing over water-cooled copper electrodes of a magnetically rotated arc plasma gun corresponding to electrodes 16 and 18. The formed gas plasma is passed as a flame into a cooled graphite-lined reactor (chamber 6) downstream of the gun. Into this plasma flame 78 grams/minute of preheated calcium fluoride is aspirated by 15 grams/minute of argon, along with 48 grams/minute of fine carbon, aspirated by 5 grams/minute of argon. The amount of carbon is 4 times that required to convert all of the fluorine in the calcium fluoride to tetrafluoroethylene. The combined argon and reactive gas plasma mixture has a temperature in the range of 6000° C. The combined gas stream exits the graphite-lined reactor into a quench chamber where the gas stream is rapidly quenched, by a spray shower of cool carbon particles which settle as a bed in the quench chamber to a temperature less than 500° C. The now solid metal related byproducts and carbon are removed by an auger for further cooling and recycle of byproducts and the residual gases are further cooled and stored for future separation, recovery, and recycle. The table below shows the compositions of the various streams from this example and are given in grams/minute. The compositions of the streams are determined by the following analyses: Since the weight of carbon particles in the quench chamber is known before starting the experiment, this weight of carbon is removed from the calculations and reported composition by material balance. The exit gases are monitored by a flow meter and are then analyzed on a gas chromatograph. A Hewlett-Packard 5880A series gas chromatograph is used for this analysis. A 20 foot long, ⅛th inch diameter, stainless steel column (from Supelco, Inc.), packed with 60/80 mesh Carbopack@ B, with 1% SP-1000 high boiling liquid, is used to separate the individual components as shown in the analysis for the example. After a sample is injected into the gas chromatograph, the temperature on the column is held constant for 5 minutes at 40° C. and then the temperature is increased to 180° C., at a rate if 20° C./minute. The area percents obtained from the thermal conductivity detector of the gas chromatograph are converted into weights and weight percents for the exit gases.

For analysis of the solid reaction products, a sample of the solids from the reactor are removed under nitrogen to a dry box for analysis. A weighed sample of the solids are placed in a jar and water is carefully added to the mixture. As the gases are evolved, their volume is measured and then the evolved gas are dried and analyzed by the gas chromatograph as listed above. The amount of calcium carbide and calcium metal are determined from the equations below by measuring the amount of acetylene and hydrogen generated.

$$CaC_2 + H_2O \rightarrow Ca(OH)_2 + C_2H_2$$

$$Ca + H_2O \rightarrow Ca(OH)_2 + H_2$$

The water is drained from the residual solids sample and the sample is placed in a vacuum tube inside of a furnace and is heated, under vacuum for two hours, to 600° C. to convert all of the $Ca(OH)_2$ to CaO. The sample in the furnace tube is cooled, removed, weighed and returned to the furnace tube where oxygen is slowly added to burn off all of the carbon. The sample is reweighed to determine the total amount of carbon removed from the sample. From this single sample the calcium, calcium carbide, and carbon have been determined, thus allowing the calculation of the amount of calcium fluoride.

| Component | Plasma Feed g/m | Solid Reaction Products g/m | Exit Gases g/m |
|---|---|---|---|
| Argon | 160 | | 160.0 |
| $CaF_2$ | 78 | 11.7 | |
| Carbon | 48 | 37.4 | |
| $CaC_2$ | | 2.7 | |

| Component | Plasma Feed g/m | Solid Reaction Products g/m | Exit Gases g/m |
|---|---|---|---|
| Calcium | | 32.3 | |
| $CF_4$ | | | 3.7 |
| $CF_2=CF_2$ | | | 34.8 |
| $C_3F_6$ | | | 1.8 |
| $C_2F_6$ | | | 0.8 |
| Misc. FC's | | | 0.8 |
| Totals | 286 | 84.1 | 201.9 |

The miscellaneous fluorocarbons are a variety of three carbon and four carbon and higher perfluorocarbons. The exit gases are available for separation and purification by both absorption and distillation so that the argon can be recycled to the plasma gun, along with any undesired perfluorocarbons or perfluoroolefins which can be recycled to the plasma flame.

EXAMPLE 2

The desired reaction sequences for this Example is as follows:

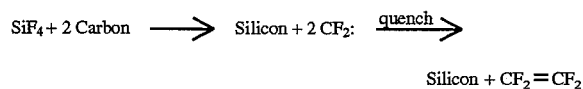

$SiF_4 + 2\, Carbon \longrightarrow Silicon + 2\, CF_2: \xrightarrow{quench}$ $Silicon + CF_2 = CF_2$ The same equipment and general procedures as outlined in Example 1 are used in this Example except that silicon tetrafluoride is fed to the plasma reactor in place of calcium fluoride. 280 grams/minute of argon is passed through the electrodes in the plasma gun. To this is added 104 grams/minute of preheated gaseous $SiF_4$, which is also used to aspirate 96 grams/minute of carbon. This amount of carbon is 4 times the stoichiometric amount needed to convert all of the fluorine in the $SiF_4$ feed stream to $CF_2$: radicals. By controlling the power input to the plasma gun, the temperature of the reactive mixture is in the range of 6000° C. The gas products, still in contact with the excess carbon, are rapidly quenched to less than 500° C. by the addition of 560 grams/minute of chilled argon and by heat losses through the walls of the associated quench chamber. The overall cooling rate is more than 10,000° C./second, but is slightly slower than was used in the previous example. The bulk of the metal related byproducts and carbon are further cooled and fall out in a knockout pot located below the quench chamber. The remaining solids are removed from the gas stream by a solids cyclone. The gaseous products stream is fed directly to an absorption/distillation train where the argon is recovered for recycle and the fluorocarbons are refined for further product uses or for recycle to the reaction chamber. The table below shows the various stream compositions for this example, listed in grams/minute, but does not include the 560 grams/minute of quench argon added to the exiting gases.

| Component | Plasma Feed g/m | Solid Reaction Products g/m | Exit Gases g/m |
|---|---|---|---|
| Argon | 280 | | 280.0 |
| $SiF_4$ | 104 | | 10.4 |
| Carbon | 96 | 76.3 | |
| Silicon | | 23.7 | |
| SiF | | 1.7 | |
| SiC | | 0.7 | |
| $CF_4$ | | | 9.5 |
| TFE | | | 67.8 |
| HFP | | | 5.8 |
| $C_2F_6$ | | | 2.4 |
| Misc. FC's | | | 1.7 |
| Totals | 480 | 102.4 | 377.6 |

Since the quench rate is slightly slower in Example 2, the ratio of TFE to all other fluorocarbons is lower (3.5/1) than in Example 1 (4.9/1). Still, the other perfluorocarbons may have added value and be a desired result. The SiF shown in Example 2 is a complex with the metal silicon recovered. In both Examples, the amount of formed metal carbide is extremely low. Again, as in Example 1, the quench carbon has been removed from the listed analysis by using a material balance over the entire solid product. The volume amount of $SiF_4$ in the exit gases is determined by double scrubbing a measured volume sample of the exit gas in water, thus removing the $SiF_4$ by the reaction:

$$3SiF_4 + 2H_2O \rightarrow 2H_2SiF_6 (\text{in water solution}) + SiO_2$$

The $SiO_2$ precipitates and stays with the water solution. The decrease in the sample volume shows the amount of $SiF_4$ in the sample. After drying the residual exit gas over calcium sulfate, the remaining gas is analyzed by Gas chromatograph as given in Example 1.

The solids from Example 2 are collected from the knockout pot and the cyclone. These solids contain carbon, silicon, SiF complex, and SiC. A sample of these solids are collected under nitrogen and analyzed in a dry box by first washing a weighed sample by slowly adding excess water to remove the SiF complex. After drying the remaining solids sample under vacuum, the weight loss is the value reported as SiF complex. The residual dried sample is placed in a furnace tube for two hours and oxygen is slowly added to burn off the carbon but the temperature is kept at below 600° C. to minimize reaction with the silicon metal. The cooled sample is removed from the furnace and weighed to determine the amount of carbon in the sample. The sample is returned to the furnace and is reacted with a flow current of dry chlorine, thus removing the silicon as silicon tetrachloride. The sample is re-weighed to determine the amount of silicon lost and the residual weight of the sample is assumed to be silicon carbide, though it may be contaminated by trace amounts of silicon dioxide.

EXAMPLE 3

The desired reaction sequence for this example is:

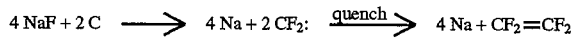

$4\, NaF + 2\, C \longrightarrow 4\, Na + 2\, CF_2: \xrightarrow{quench} 4\, Na + CF_2 = CF_2$ The equipment for this example consists of a plasma gun, being fed 160 grams/minute of argon. The flame from this torch is contained in an externally cooled graphite reactor, where 84 grams/minute of sodium fluoride and 24 grams/minute of −200 mesh carbon powder are added. The amount of carbon is twice that necessary to convert all of the fluorine in the sodium fluoride to tetrafluoroethylene. The temperature at the exit of the reaction chamber is in the range of 5000° C. The gases are expanded into a larger graphite lined chamber where approximately 2400 grams/minute of cooled recycle gas is added to the hot gases to rapidly quench the entire stream to less than 400° C. The entire process stream is further cooled to below 100° C. and the solidified carbon, sodium and remaining sodium fluoride are collected in a cyclone and filter system. The sodium and sodium fluoride in this mixed product could later be recovered from the carbon by reheating the mixture. The gas stream from this system can be further cooled and used as the quenching gas or may be refined for recovery and/or recycle to the plasma reactor. The Table below shows the results from this experiment. Thus, 84% of the sodium fluoride was converted. Of the liberated fluorine, 81% ended up as TFE. The other fluorocarbons could be recovered for other uses or recycled for conversion to TFE. The data in the Table is presented on a recycle free basis. The sodium fluoride, sodium, and carbon in the Table for this example are all solids and a sample, collected from the cyclone and filter system is transferred under nitrogen to a dry box. The sample is weighed and then analyzed by placing it is a jar where water is very slowly added to the mixture, being aware of the hazardous potential of the reaction of sodium and water. The volume of liberated hydrogen is measured and and the amount of sodium in the sample is calculated from the reaction shown below:

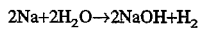

2Na+2H$_2$O→2NaOH+H$_2$

Since sodium fluoride and sodium hydroxide are both soluble in the water, excess water is used to remove both of them from the sample. The residual sample is dried under vacuum and re-weighed to determine the amount of carbon in the sample.

The residual gases which separate from the solids in the product stream, are analyzed as in Example 1, after being metered through a gas flow meter.

| Component | Feed Materials gm/min | Product Stream gm/min |
|---|---|---|
| Argon | 160 | 160.0 |
| NaF | 84 | 13.4 |
| Carbon | 24 | 14.5 |
| Sodium | — | 38.7 |
| TFE | — | 33.9 |
| CF$_4$ | — | 3.4 |
| C$_2$F$_6$ | — | 1.9 |
| C$_3$F$_6$ | — | 1.7 |
| Misc. | — | 0.5 |
| Totals | 268 | 268.0 |

EXAMPLE 4

The equipment used in this example is similar to that used in Example 3 except that the plasma gun is pointed in an upward direction and the quenching is performed by a fluidized bed of carbon. The analysis shown for this Example is given on a basis that is free of this quench carbon, as determined by material balance. The flow of gases into the quench chamber is controlled by a pointed check valve that opens the fluidized bed to the plasma gases when there is a positive flow of gas. A portion of the product gases are recirculated to help fluidize the bed. An internal tinned water-cooled heat exchanger is used to keep the fluidized carbon and the product gases at a temperature of less than 350° C. A cyclone returns any carry-over of fines to the fluid bed. The silicon, as it is cooled, coats the carbon so a purge stream of coated carbon particles is removed from the bed for the recovery of silicon and other metal products. The bed is replenished by the addition of more carbon particles. The desired reaction sequence would be:

$$SiF_4 + 2C \longrightarrow Si + 2CF_2: \xrightarrow{quench} Si + CF_2=CF_2$$

For each mol of silicon tetrafluoride fed to the system, 6 mols of argon were fed to the plasma gun. The −200 mesh carbon was also fed to the plasma flame at 2X that required to convert all of the fluorine into TFE. The excess carbon was blown, along with the hot gases, into the quench bed and most of it was removed as fines from the cyclone for reprocessing. The gases exiting the quench chamber were further cooled for analysis and then could be separated for product or recycle. The Table below shows the material balance around the process, excluding any recycle gases. The miscellaneous component included all other fluorocarbons except those listed. After cooling and separating the solids from the gases, the products are analyzed as in Example 2. In Example 4, there is only an unrecorded trace of SiC.

| Component | Feed Materials gm/min | Product Stream gm/min |
|---|---|---|
| Argon | 240 | 240.0 |
| SiF$_4$ | 104 | 12.5 |
| Carbon | 48 | 28.7 |
| SiF | — | 3.0 |
| Silicon | — | 22.8 |
| TFE | — | 68.3 |
| CF$_4$ | — | 7.7 |
| C$_2$F$_6$ | — | 4.7 |
| C$_3$F$_6$ | — | 2.6 |
| Misc. | — | 1.7 |
| Totals | 392 | 392.0 |

What is claimed is:

1. The process for the manufacture of tetrafluoroethylene (TFE) comprising forming an extended turbulent plasma having an undefined portion, dissociating non-carbonaceous metal fluoride into a gaseous mixture of metal and reactive fluorine in the presence of carbon in the unconfined portion of said plasma to form a precursor to TFE, and quenching said precursor to obtain as a result thereof said TFE, said dissociating being carried out in the absence of halogen other than fluorine.

2. The process of claim 1 wherein the said reaction temperature is at least 3800° C.

3. The process of claim 1 wherein the reaction mixture is quenched to less than 500° C.

4. The process of claim 1 wherein the metal fluoride is a silicon fluoride.

5. The process of claim 1 wherein the metal fluoride is calcium fluoride.

6. The process of claim 1 wherein said metal fluoride is sodium fluoride.

7. The process of claim 1 wherein said quenching causes said metal of said gaseous mixture to condense as a liquid or as a solid.

8. The process of claim 7 wherein said metal is silicon, calcium, or sodium.

9. The process of claim 1 wherein at least one atom of carbon is present for each two atoms of fluorine provided by said metal fluoride.

10. The process of claim 1 wherein said carbon is present in a stoichiometric excess with respect to said reactive fluorine.

11. The process of claim 1 wherein said plasma is formed from an inert gas and said metal fluoride and carbon are fed into said unconfined portion of said plasma.

12. The process of claim 1 wherein said forming of said plasma is by passing gas through an electric arc struck between non-consumable electrodes.

13. The process of claim 1 wherein said quenching is done by contacting said precursor to TFE with cool particles.

14. The process of claim 13 wherein said metal from said metal fluoride condenses on said particles.

15. The process of claim 14 wherein said particles are of the same metal as the metal of said metal fluoride.

16. Process comprising contacting and reacting non-carbonaceous metal fluoride with carbon in an unconfined plasma flame to form a gaseous mixture which contains metal and the combination of fluorine and carbon which is capable of being quenched to form tetrafluoroethylene, said reacting being carried out in the absence of halogen other than fluorine.

17. The process of claim 1 wherein the reaction is carried out at a pressure of at least 300 mm Hg.

18. Process of claim 16 wherein said metal fluoride is fed to said flame.

19. Process of claim 16 wherein said carbon is in the form of particles and said carbon particles are fed to said flame.

20. Process of claim 19 wherein said metal fluoride is fed to said flame and said flame is formed from a gas other than from said metal fluoride and said carbon.

21. Process of feeding non-carbonaceous metal fluoride and carbon to an unconfined plasma flame to form a gaseous reaction mixture which is capable of being quenched to form tetrafluoroethylene, and quenching said gaseous reaction mixture to obtain as a result thereof said tetrafluoroethylene, said feeding being carried out in the absence of halogen other than fluorine.

* * * * *